United States Patent [19]

Illingsworth, deceased

[11] E Re. 29,575

[45] Reissued Mar. 14, 1978

[54] CUBIC REGULAR GRAIN PHOTOGRAPHIC REVERSAL EMULSIONS

[75] Inventor: Bernard D. Illingsworth, deceased, late of Rochester, N.Y., by Eastman Kodak Company

[73] Assignee: Eastman Kodak Company, Rochester, N.Y.

[21] Appl. No.: 782,812

[22] Filed: Mar. 30, 1977

Related U.S. Patent Documents

Reissue of:

[64] Patent No.: 3,501,306
Issued: Mar. 17, 1970
Appl. No.: 619,909
Filed: Mar. 2, 1967

U.S. Applications:

[63] Continuation-in-part of Ser. No. 533,400, Mar. 11, 1966, abandoned.

[51] Int. Cl.[2] ..... G03C 1/36; G03C 1/28

[52] U.S. Cl. ..... 96/101; 96/94 R; 96/107

[58] Field of Search ..... 96/101, 107, 94 R

[56] References Cited

FOREIGN PATENT DOCUMENTS

| | | |
|---|---|---|
| 1,169,290 | 4/1964 | Germany. |
| 723,019 | 2/1952 | United Kingdom. |

OTHER PUBLICATIONS

Klein et al., "Ia Properties of Photographic Emulsion Grains," Journal of Photographic Science, vol. 12, pp. 242–244, (1964).

Moisar et al., "Investigation of the Topography of Latent Interior and Exterior Images," Bunsengesellschaft for Physickalische Chemie. Berichte 67, No. 4, pp. 356–359, (1963).

*Primary Examiner*—J. Travis Brown
*Attorney, Agent, or Firm*—Carl O. Thomas

[57] ABSTRACT

Direct-positive photographic emulsions comprising silver halide grains which have a substantially regular crystal shape in contrast to substantially irregular crystal shape, are disclosed. Such emulsions can contain electron acceptors and the grains can be fogged with both reduction and gold fogging agents. Photographic elements employing such emulsions and processes for preparing them are also disclosed.

33 Claims, No Drawings

CUBIC REGULAR GRAIN PHOTOGRAPHIC REVERSAL EMULSIONS

Matter enclosed in heavy brackets [ ] appears in the original patent but forms no part of this reissue specification; matter printed in italics indicates the additions made by reissue.

This application is a continuation-in-part of Illingsworth U.S. application Ser. No. 533,400, filed Mar. 11, 1966 and entitled "Direct-Positive Photographic Emulsions[."]," *now abandoned.*

This invention relates to photographic materials, their preparation and use. In one of its aspects, this invention relates to direct-positive photographic emulsions and elements comprising fogged silver halide grains and a compound which accepts electrons. In another of its aspects, this invention relates to direct-positive photographic silver halide emulsions and elements comprising reduction and gold fogged silver halide grains having a regular structure.

It is known that direct-positive images can be obtained with certain types of photographic silver halide reversal emulsions. As shown in British Patent 723,019, published Feb. 2, 1955, one photographic emulsion of this type is a photographic emulsion comprising an electron trapping compound and silver halide grains which are fogged with a combination of a reducing agent and a gold compound or a compound of a metal more electro-positive than silver, such as, for example, palladium or platinum. However, in the past, direct-positive photographic silver halide emulsions comprising fogged silver halide grains, particularly those silver halide grains fogged using a combination of fogging agents as disclosed in British Patent 723,019, have not exhibited the high speed required for many applications in photography. It is evident, therefore, that a means for increasing the photographic speed of direct-positive photographic emulsions comprising fogged silver halide grains would substantially enhance the art.

Accordingly, it is an object of this invention to provide direct-positive photographic emulsions exhibiting increased photographic speed.

Another object of this invention is to provide a means for obtaining fogged direct-positive photographic silver halide emulsions and elements which comprise regular silver halide grains.

Still another object of this invention is to provide a means for obtaining fogged direct-positive photographic silver halide emulsions and elements comprising electron trapping compounds such as cyanine dyes.

Still another object of this invention is to provide improved photographic reversal emulsions obtained by combining a low level of reduction and gold fogging of photographic silver halide grains having a regular structure.

Other objects and advantages of the invention will become apparent from an examination of the specification and claims which follow.

In accordance with this invention, it has been found that the above and other objects of this invention can be obtained with direct-positive photographic emulsions comprising fogged silver halide grains having a regular crystal shape. Silver halide grains which have a regular crystal shape, as contrasted to an irregular crystal shape, are well known, as shown, e.g., in Ch. 2 of "The Theory of the Photographic Process," Mees and James, 3rd ed. (1966), published by the Macmillan Co. The regular grain direct-positive photographic silver halide emulsions of this invention exhibit a significant increase in photographic speed or sensitivity in comparison to direct-positive photographic silver halide emulsions in which the silver halide grains do not have a regular crystal shape.

One embodiment of this invention relates to a direct-positive photographic emulsion comprising fogged silver halide grains, at least 80%, by weight, of said grains being regular.

Another embodiment of this invention relates to a direct-positive photographic emulsion comprising reduction and gold fogged silver halide grains and a compound which accepts electrons, at least 80%, by weight, of said grains being regular.

Another embodiment of this invention relates to a photographic element comprising a support and at least one photographic silver halide layer which comprises fogged silver halide grains, at least 80%, by weight, of said grains being regular.

Another embodiment of this invention relates to a photographic element comprising a support and at least one photographic silver halide layer which comprises reduction and gold fogged silver halide grains and a compound which accepts electrons, at least 80%, by weight, of said grains being regular and the concentration of reduction fogging agent employed to fog said grains being in the range of about 0.0005 to 0.06 milliequivalents per mole of silver halide.

Still another embodiment of this invention relates to the process which comprises contacting (1) silver halide grains, at least 80%, by weight, of which are regular, and (2) about 0.0005 to about 0.06 milliequivalents per mole of silver halide of a reduction fogging agent and about 0.001 to about 0.01 millimoles per mole of silver halide of a gold fogging agent, (3) at a temperature in the range of about 40 to about 100° C., the ratio of gold fogging agent to reduction fogging agent being in the range of about 1:3 to about 20:1.

The regular grain, fogged direct-positive photographic emulsions of this invention comprise silver halide grains which are regular in structure or shape. These emulsions can contain some fogged silver halide grains which are not regular. However, when such grains are present, they generally do not constitute more than about 20%, by weight, of the grains smaller than the mean grain size and/or more than about 20%, by number, of the grains larger than the mean grain size. Preferred direct-positive emulsions of this invention comprise fogged silver halide grains of which at least about 80%, often at least about 90 or 95%, by weight, are regular. Silver halide emulsions in which a major portion of the grains have a regular structure or shape are known. As disclosed in a paper entitled "Fundamental Aspects of Growth and Shape of Photographic Silver Halide Crystals," published in The Proceedings of the 5th International Conference on Nuclear Photography held at Cern, Geneva, Sept. 15–18, 1965, edited by E. Dahl-Jensen; regular silver halide grains or crystals are obtained by isotropic growth occurring simultaneously and uniformly on all crystal faces. Such crystals develop (1,0,0) or (1,1,1) faces and are free of twin plane stacking faults, e.g., twin planes such as (1,1,1) twin planes. A (1,1,1) twin plane is a stacking fault which arises when a silver halide crystal grows in such a manner as to alter the previously established order of stacking of (1,1,1) planes in forming the crystal.

Photographic silver halide emulsions comprising silver halide grains of regular shape or structure can be obtained by controlling the reaction conditions during the phase of crystal growth. Depending upon these conditions the regular silver halide grains will be characterized by a certain crystal habit, e.g., cubic, cubo-octahedral and/or octahedral, and will exhibit certain planes, e.g., (1,0,0) or (1,1,1) planes, as crystal faces. For example, in an article entitled "Precipitation of Twinned AgBr Crystals," by Berry and Skillman, Photographic Science and Engineering, vol. 6, No. 3, May–June 1962; it is shown that by a change in pAg it is possible to conduct a double-run precipitation of silver halide in such a manner that regular cubes or octahedra are formed. In a double run procedure, the silver halide grains are prepared by simultaneously running an aqueous solution of a water soluble silver salt, for example, silver nitrate, and a water soluble halide, for example, an alkali metal halide such as potassium bromide, into a rapidly agitated aqueous solution of a silver halide peptizer, preferably gelatin, a gelatin derivative or some other protein peptizer. To obtain substantially regular grains a large excess of halide ion is generally avoided. As disclosed hereinbefore the conditions employed during the preparation of the silver halide grains are inter-related and a change in one variable such as pAg, pH, etc., while maintaining other conditions constant can change the silver halide crystal structure as shown, e.g., in Example I which follows. However, the temperature is generally in the range of about 30 to about 90° C., the pH is up to about 9.7, preferably 4 or less and the pAg is up to about 9.8. In addition to previous references, a suitable method for preparing photographic silver halide emulsions having the required regular shape is also disclosed in an article entitled, "Ia: Properties of Photographic Emulsion Grains," by Klein and Moisar, The Journal of Photographic Science, vol. 12, 1964, pp. 242–251. A preferred class of photographic silver halide emulsions employed in the practice of this invention contains silver halide grains in which (1,0,0) faces predominate. Such silver halide grains are referred to herein as "cubic regular" grains. These cubic regular grains can be prepared by carrying out the aforementioned double run procedure so that the pAg is maintained at a value in the range of about 7.1 to about 9.2. The pAg employed can change with the particular silver halide prepared. For example, the silver bromides are generally prepared at a pAg in the range of about 8.6 to about 9.2, the silver chlorobromides at about 7.9 and the silver chlorides at about 7.1. The pH is maintained at about 4 or less during the preparation with sulfuric or an equivalent acid. Quantities of halide ion greatly in excess of silver ion in the mass are also avoided.

The regular silver halide grains in the direct-positive photographic emulsions of this invention are *reduction and gold* fogged. Fogging can be effected by chemically or physically treating the photographic silver halides by methods previously described in the prior art. Such fogging can be accomplished by various techniques such as chemical sensitization to fog, particularly good results being obtained with techniques of the type described by Antoine Hautot and Henri Saubenier in Science et Industries Photographiques, vol. XXVIII, January 1957, pp. 57 to 65. The silver halide grains can be [fogged with high intensity light,] reduction fogged with a reducing agent such as thiourea dioxide or stannous chloride or fogged with gold [or noble metal compounds]. Combinations of reduction fogging agents with gold compounds [or compounds of another metal more electropositive than silver, e.g., rhodium, platinum or iridium,] can be used in fogging the silver halide grains. The fogged silver halide grains in the direct-positive photographic emulsions of this invention give a density of at least 0.5, when developed without exposure for five minutes at 68° F., in Kodak DK-50 Developer when a direct-positive emulsion containing such grains is coated at a coverage of 50 to about 500 mg. of silver per square foot of support.

The direct-positive photographic emulsions of this invention can comprise reduction and gold fogged silver halide grains, e.g., cubic regular, cubo-octahedral regular and/or octahedral regular silver halide grains which are fogged with a combination of a reduction fogging agent and a gold fogging agent. When a low concentration of gold and reducing agent is employed in such a combination the fogged silver halide grains are characterized by a rapid loss of fog upon chemical bleaching, as described hereinafter. It is well known that one equivalent weight of a reducing agent will reduce one equivalent weight of silver halide to silver. To obtain the fogged silver halide grains which are characterized by a rapid loss of fog upon bleaching, much less than one equivalent weight of reduction fogging agent is employed. Thus, less than about 0.06 milliequivalent of reduction fogging agent per mole of silver halide is employed in fogging the silver halide grains. Generally, about 0.0005 to about 0.006, preferably about 0.001 to about 0.03 milliequivalent of reduction fogging agent per mole of silver halide is employed in fogging the silver halide grains in the practice of this invention. Higher concentrations of reduction fogging agent can result in a substantial loss in photographic speed. A preferred reduction fogging agent employed in combination with the gold fogging agent, or a component of another metal more electropositive than silver, is thiourea dioxide which is preferably employed at a concentration in the range of about 0.05 to about 3, most preferably about 0.1 to about 2 milligrams per mole of silver halide or about 0.0005 to about 0.03 millimole per mole of silver halide. Stannous chloride is another suitable reduction fogging agent which is used in practicing this invention and is preferably used in concentrations in the range of about 0.05 to about 3 milligrams of stannous chloride per mole of silver halide. The use of the reduction and gold fogging agents in low concentrations gives direct-positive photographic silver halide emulsions exhibiting outstanding photographic speed. Examples of suitable reduction fogging agents which can be employed in the practice of this invention include hydrazine, phosphonium salts such as tetra(hydroxy methyl) phosphonium chloride, thiourea dioxide, as disclosed in Hillson U.S. Patent 3,062,651, issued Nov. 6, 1962, and Allen et al. U.S. Patent 2,983,609, issued May 9, 1961, reducing agents such as stannous salts, e.g., stannous chloride, as disclosed in Carroll U.S. Patent 2,487,850, issued Nov. 15, 1939, polyamines such as diethylene triamine, as disclosed in Lowe et al., U.S. Patent 2,519,698, issued Aug. 15, 1950, polyamines such as spermine as disclosed in Lowe et al., U.S. Patent 2,521,925, filed Sept. 12, 1950, bis($\beta$-aminoethyl)sulfide and its water soluble salts as disclosed in Lowe et al., U.S. Patent 2,521,926, issued Sept. 12, 1950, and the like. The gold fogging agents employed in practicing this invention can be any gold salt suitable for use in fogging photographic silver halide grains and includes the gold salts disclosed in Waller et al., U.S. Patent 2,399,083, issued Apr. 23, 1946, and Damschroder et al., U.S. Patent 2,642,361 issued June 16, 1953. Specific examples of gold fogging agents are potassium chloroaurite, potassium aurithlocyanate, potassium chloroaurate, auric trichloride 2-aurosulfobenzothiazole metho chloride, and the like. The concentration of gold fogging agent employed in the practice of this invention is subject to variation, but is generally in the range of about 0.001 to about 0.01 millimole per mole of silver halide. Potassium chloroaurate is a preferred gold fogging agent and is often used at concentrations of less than about 5 mg. per mole of silver halide and preferably at concentrations in the range of about 0.5 to about 4 milligrams per mole of silver halide. When a gold fogging agent is used in combination with a reduction fogging agent, the gold fogging agent preferably comprises a major portion of the fogging combination with the ratio of gold fogging agent to reduction fogging agent generally being in the range of about 1:3 to about 20:1, often about 2:1 to about 20:1. The silver halide grains are preferably fogged using the reduction fogging agent initially and subsequently using the gold fogging agent. However, the reverse order of agents can be used or the reduction and gold fogging agents can be used simultaneously.

In practicing this invention, the silver halide grains can be fogged prior to coating or they can be coated prior to fogging. The reaction conditions during fogging of the silver halide grains are subject to wide variation although the pH is generaly in the range of about 5 to about 7, the pAg is generally in the range of about 7 to about 9 and the temperature is generally in the range of about 40 to about 100° C., most often about 50 to about 70° C. During fogging the silver halide grains can be suspended in a suitable vehicle such as gelatin which is generally employed at a concentration in the range of about 50 to about 200 grams per mole of silver halide.

As previously indicated, the most desirable photographic speed is exhibited by direct-positive photographic emulsons comprising regular silver halide grains which are fogged using a combination of a reduction fogging agent with a gold fogging agent at low concentration. Such silver halide grains are characterized by a rapid loss of fog upon chemical bleaching. These grains will lose at least about 25% and generally at least about 40% of their fog when bleached for ten minutes at 68° F., in a potassium cyanide bleach composition as described hereinafter. This fog loss can be illustrated by coating the regular silver halide grains as a photographic silver halide emulsion on a support to give a maximum density of at least 1.0 when processed for 6 minutes at about 68° F., in Kodak DK-50 developer and comparing the density of such a coating with an identical coating which is processed for 6 minutes at 68° F., in Kodak DK-50 developer after being bleached for about 10 minutes at 68° F., in the potassium cyanide bleach composition. The maximum density of the unbleached coating will be at least 30% greater, generally at least 60% greater than the maximum density of the bleached coating. Kodak DK-50 developer is described in the "Handbook of Chemistry and Physics," 30th ed., 1947, Chemical Rubber Publishing Co., Cleveland, Ohio, p. 2558, and has the following composition:

Water, about 125° F. (52° C.)—500 cc.
N-methyl-p-aminophenol sulfate—2.5 grams
Sodium sulfite, desiccated—30.0 grams
Hydroquinone—2.5 grams
Sodium metaborate—10.0 grams
Potassium bromide—0.5 gram
Water to make 1.0 liter One embodiment of this invention relates to direct-positive photographic emulsions which comprise not only regular silver halide grains, but also a compound which accepts electrons. Suitable electron accepting compounds include the photoelectron accepting compounds or desensitizing dyes often used in photographic reversal systems. Compounds of this type include the known desensitizers which trap electrons, as disclosed in British Patent 723,019, published Feb. 2, 1955. The electron acceptors which give particularly good results in the practice of this invention can be characterized in terms of their polarographic halfwave potentials, i.e., their oxidation reduction potentials determined by polarography. Cathodic measurements can be made with a $1\times10^{-4}$ molar solution of the electron acceptor in a solvent, for example, methanol which is 0.05 molar in lithium chloride using a dropping mercury electrode with the polarographic halfwave potential for the most positive cathodic wave being designated $E_c$. Anodic measurements can be made with $1\times10^{-4}$ molar aqueous solvent solution, for example methanolic solutions of the electron acceptor which are 0.05 molar in sodium acetate and 0.005 molar in acetic acid using a carbon paste of pyrolytic graphite electrode, with the voltommetric half peak potential for the most negative anodic response being designated $E_a$. In each measurement, the reference electrode can be an aqueous silver-silver chloride (saturated potassium chloride) electrode at 20° C. Electrochemical measurements of this type are known in the art and are described in New Instrumental Methods in Electrochemistry, by Delahay, Interscience Publishers, New York, N.Y., 1954; Polarography, by Kolthoff and Lingane, 2nd ed., Interscience Publishers, New York, N.Y., 1952; Analytical Chemistry, 36, 2426 (1964) by Elving; and Analytical Chemistry, 30, 1576 (1958) by Adams. Plus and minus signs are according to IUPAC (International Union of Pure and Applied Chemistry) Stockholm Convention 1953. Compounds which can be employed as electron acceptors in the practice of this invention include organic compounds having anodic polarographic halfwave potential ($E_a$) and a cathodic polarographic potential ($E_c$) which when added together give a positive sum. Preferably, such compounds also spectrally sensitize photographic silver halide emulsions to radiation having a wavelength of at least about 480 mμ and generally spectrally sensitize such emulsions in the range of about 480 to about 800 mμ. Advantageously, these compounds provide spectral sensitization such that the ratio of minus blue relative speed to blue relative speed is greater than 7 and preferably greater than 10 when exposed to a tungsten light source through Wratten No. 16 and No. 35 plus 38A filters respectively, and can be termed "spectral sensitizing electron acceptors."

An especially useful class of electron accepting compounds which can be used in the direct-positive photographic silver halide emulsions of this invention are cyanine dyes, particularly imidazoquinoxaline dyes such as those disclosed in Brooker et al. Belgian Patent 660,253, published Mar. 15, 1965. Very good results are obtained with cyanine dyes containing an indole nucleus aromatically substituted in the 2 position, i.e., a cyanine dye containing a 2-aromatically substituted indole nucleus. One useful class of spectral sensitizing electron acceptors are the bis(1-alkyl-2-phenyl indole-3) trimethine cyanines described by Coenen et al., U.S. Patent 2,930,694, issued Mar. 29, 1960. Another useful class of dimethine cyanine dyes of this type is disclosed in British Patent 970,601.

Still another class of useful spectral sensitizing electron acceptors are the cyanine and merocyanine dyes in which at least one nucleus and preferably two nuclei, contain desensitizing substituents such as $NO_2$, e.g., 3,3'-diethyl-6,6α-dinitrothiacarbocyanine chloride, as shown in British Patent 723,019.

The compounds which accept electrons in the direct-positive photographic silver halide emulsions of this invention can be employed in widely varying concentrations. However, such compounds are preferably employed at concentrations in the range of about 100 milligrams to about 2 grams of electron acceptor per mole of silver halide. Specific examples of suitable electron acceptors include;

(1) 1,1-dimethyl-2,2'-diphenyl-3,3'-indolocarbocyanine bromide

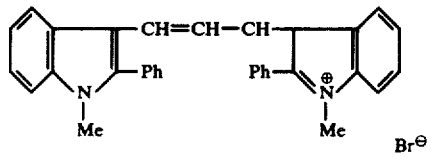

(2) 2,2'-di-p-methoxyphenyl-1,1'-dimethyl-3,3'-indolocarbocyanine bromide

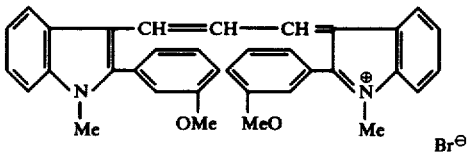

(3) 1,1'-dimethyl-2,2'-δ-triphenyl-3,3'-indolocarbocyanine perchlorate

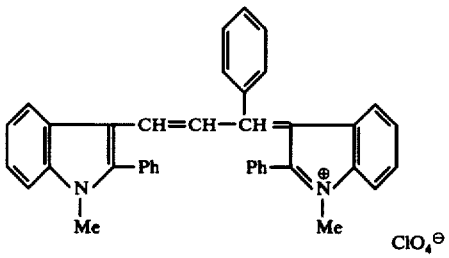

(4) 1,1',3,3'-tetraethylimidazo[4,5-b]quinoxalinocarbocyanine chloride

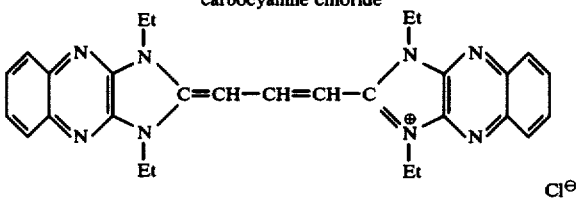

Additional examples include phenosafranine, pinacryptol yellow, 5-m-nitrobenzylidenerhodanine, 5-m-nitrobenzylidene-3-phenylrhodanine, 3-ethyl-5-m-nitrobenzylidenerhodanine, 3-ethyl-5-(2,4-dinitrobenzylidene) rhodanine, 5-o-nitrobenzylidene-3-phenylrhodanine, 1',3-diethyl-6-nitrothia-2'-cyanine iodide, 6-chloro-4-nitro-benzotriazole, 3,3'-diethyl-6,6α-dinitro-9-phenylthiacarbocyanine iodide, 2-(p-dimethylaminophenylimino-methyl)benzothiazole ethoethyl sulfate, crystal violet, 3,3'-diethyl-6,6'-dinitrothiacarbocyanine ethyl sulfate, 1',3-diethyl-6-nitrothia-2'-cyanine iodide, 1,3-diamino-5-methylphenazinium chloride 4-nitro-6-chlorobenzotriazole, 3,3'-di-p-nitrobenzylthiacarbocyanine bromide, 3,3'-di-p-nitrophenylthiacarbocyanine iodide, 3,3'-di-o-nitrophenylthiacarbocyanine perchlorate, 3,3'-dimethyl-9-trifluoromethylthiacarbocyanine iodide, 9-(2,4-dinitrophenylmercapto)-3,3'-diethylthiacarbocyanine iodide, Bis (4,6-diphenylpyryl-2)trimethinecyanine perchlorate, anhydro-2-p-dimethylaminophenyliminomethyl-6-nitro-3-(4-sulfobutyl)-benzothiazolium hydroxide, 1-(2-benzothiazolyl)-2-(p-dimethylaminostyryl)-4,6-diphenylpyridinium iodide, 1,3-diethyl-5-[1,3-neopentylene-6-(1,3,3-trimethyl-2-indolinylidene)-2,4-hexadienylidene]-2-thiobarbituric acid, 2,3,5-triphenyl-2H-tetrazolium chloride, 2-(4-iodophenyl)-3-(4- -nitrophenyl)- 5-phenyl-tetrazolium chloride, 1-methyl-8-nitroquinolinium methyl sulfate, 3,6-Bis[4-(3-ethyl-2-benzothiazolinylidene)-2-butenylidene]-1,2,4,5-cyclohexanetetrone, and the like.

The silver halides employed in the preparation of the photographic compositions described herein include any of the photographic silver halides as exemplified by silver bromide, silver iodide, silver chloride, silver chlorobromide, silver bromoiodide, silver chlorobromide, and the like. Silver halide grains having a mean grain diameter, i.e., an average grain size in the range of about 0.1 to about 2 microns, preferably about 0.2 to about 1 micron give particularly good results. The silver halide grains are regular in shape or structure and preferably have a rather uniform diameter frequency distribution. For example, at least 95%, by weight, of the photographic silver halide grains can have a diameter which is within about 40%, preferably with 30%, of the mean grain diameter. Mean grain diameter, i.e., average grain size, can be determined using conventional methods, e.g., such as by measuring projective area as shown in an article by Trivelli and Smith entitled "Empirical Relations Between Sensitometric and Size-Frequency Characteristics in Photographic Emulsion Series," in The Photographic Journal, vol. LXXIX, 1939, pp. 330–338. Preferred photographic silver halide emulsions comprise at least 50 mole percent bromide, the most preferred emulsions being silver bromoiodide emulsions, particularly those containing less than about ten mole percent iodide. The photographic silver halides can be coated at silver coverages in the range of about 50 to about 500 milligrams of silver per square foot of support.

Various colloids can be used as vehicles or binding agents in the direct-positive photographic materials of this invention. Satisfactory colloids which can be used for this purpose include any of the hydrophilic colloids generally employed in the photographic field, including, for example, gelatin, colloidal albumin, polysaccharides, cellulose derivatives, synthetic resins such as polyvinyl compounds, including polyvinyl alcohol derivatives, acrylamide polymers and the like. In addition to the hydrophilic colloids, the vehicle or binding agent can contain dispersed polymerized vinyl compounds, particularly those which increase the dimensional stability of photographic materials. Suitable compounds of this type include water-insoluble polymers of alkyl acrylates or methacrylates, acrylic acid, sulfoalkyl acrylates or methacrylates and the like.

The photographic compositions described herein can be coated on a wide variety of supports in preparing photographic elements. The photographic silver halide emulsions can be coated on one or both sides of the support which is preferably transparent and/or flexible. Typical supports are cellulose nitrate film, cellulose ester film, polyvinyl acetal film, polystyrene film, polyethylene terephthalate film and other polyester film as well as glass, paper, metal, wood and the like. Supports such as paper which are coated with α-olefin polymers, particularly polymers of α-olefins containing two or more carbon atoms, as examplified by polyethylene, polypropylene, ethylene butene copolymers and the like, give good results.

The photographic silver halide emulsion and other layers present in the photographic elements made according to the invention can be hardened with any suitable hardener, including aldehyde hardeners such as formaldehyde and mucochloric acid, aziridine hardeners, hardeners which are derivatives of dioxane, oxypolysaccharides, such as oxy starch or oxy plant gums, and the like.

The photographic silver halide emulsion layers can contain additional additives, particularly those known to be beneficial in photographic emulsions, including, for example, lubricating materials, stabilizers, speed increasing materials, absorbing dyes, plasticizers, and the like. These photographic emulsions can also contain spectral sensitizing dyes in addition to the electron accepting compounds which can spectrally sensitize in some cases. Suitable spectral sensitizers include the cyanines, merocyanines, complex(trinuclear)cyanines, complex(trinuclear)merocyanines, styryls and hemicyanines. Furthermore, these emulsions can contain color forming couplers or can be developed in solutions containing couplers or other color generating materials. The color forming couplers can be incorporated into the direct-positive photographic silver halide emulsion using any suitable technique, e.g., techniques of the type shown in Jelley et al., U.S. Patent 2,322,027, issued June 15, 1943; Fierke et al., U.S. Patent 2,801,171, issued July 30, 1957; Fischer U.S. Patents 1,055,155 and 1,102,028, issued Mar. 4, 1913 and June 30, 1914, respectively, and Wilmanns U.S. Patent 2,186,849, issued Jan. 9, 1940. They can also be developed using incorporated developers such as polyhydroxybenzenes, aminophenols, 3-pyrazolidones, and the like.

It is sometimes advantageous to employ surface active agents or compatible mixtures of such agents in the preparation of the photographic materials described herein. Suitable agents of this type include non-ionic, ionic and amphoteric types, as exemplified by polyoxyalkylene derivatives, amphoteric amino acid dispersing agents, including sulfobetaines, and the like. Such surface active agents are described in U.S. Patent 2,600,831, issued June 17, 1952; U.S. Patent 2,271,622, issued Feb. 3, 1942; U.S. Patent 2,271,623, issued Feb. 3, 1942; U.S. Patent 2,275,727, issued Mar. 10, 1942; U.S. Patent 2,787,604, issued Apr. 2, 1957; U.S. Patent 2,816,920, issued Dec. 17, 1957; U.S. Patent 2,739,891, issued Mar. 27, 1956 and Belgian Patent 652,862.

This invention can be further illustrated by the following examples of preferred embodiments thereof although it will be understood that these examples are included merely for purposes of illustration and are not intended to limit the scope of the invention unless otherwise specifically indicated.

EXAMPLE I

Direct-positive photographic emulsions comprising regular silver halide grains exhibit substantial increases in photographic speed in comparison to direct-positive photographic silver halide emulsions comprising silver halide grains that are not regular. To illustrate, the following photographic silver halide emulsions are prepared:

Emulsion A

A cubo-octahedral regular silver bromoiodide photographic emulsion containing approximately 2.5% iodide and having an average grain size of about 0.2 micron is prepared by adding (1) an aqueous solution of potassium bromide and potassium iodide and (2) an aqueous solution of silver nitrate, simultaneously to a rapidly agitated aqueous gelatin solution at a temperature of 70° C., over a period of about 35 minutes. The pH is maintained at about 2 during precipitation and the pAg is about 9.4. The emulsion is chill-set, shredded and washed by leaching with cold water in the conventional manner. As shown by electron micrographs, over 80%, by weight, of the silver halide grains are free of twin planes. Furthermore, less than 20%, by number, of the silver halide grains larger than the mean grain size are free of twin planes, i.e., have a regular shape.

Emulsion B

A silver halide photographic emulsion in which the silver halide grains are non-regular is prepared using the procedure employed for Emulsion A except that the pH is maintained at 8 during the silver halide grain formation. The resulting emulsion has an average grain size of approximately 0.2 micron but over 90%, by weight, of the silver halide grains exhibit twin plane stacking faults.

Each of the photographic Emulsions A and B is reduction and gold fogged by first adding 0.2 mg. of thiourea dioxide and heating for 60 minutes at 65° C., and then adding 4.0 mg. of potassium chloroaurate and heating for 60 minutes at 65° C. One-hundred mg. of an electron accepting compound (5-m-nitrobenzylidenerhodanine) per mole of silver halide is added to each emulsion. Samples of each of the Emulsions A and B are coated on cellulose acetate film support at coverages of 100 mg. of silver and 250 mg. of gelatin per square foot of support. A sample of each coating is exposed on an Eastman Ib sensitometer, developed for 6 minutes in Kodak DK-50 developer, fixed, washed and dried. The maximum density, photographic speed at a given density below maximum density and gamma are determined using the same procedure for each coating. The results are as follows:

TABLE 1

| Emulsion coating | $D_{max}$ | Relative speed | Gamma |
|---|---|---|---|
| A | 1.8 | 170 | 1.8 |
| B | 1.76 | 100 | 1.6 |

It can be seen from the above results that the use of regular silver halide grains in fogged direct-positive photographic silver halide emulsions (Emulsion Coating A) gives a substantial increase in photographic speed.

Similar results are obtained when the above procedure is repeated with fogging agents, such as hydrazine, tetra(hydroxymethyl)phosphonium chloride, triethylenetetramine and gold or noble metal fogging agents such as potassium aurithiocyanate, 2-aurosulfobenzothiazole metho chloride, ammonium hexachloropalladate $[(NH_4)_2PdCl_6]$ and the like.

EXAMPLE II

The direct-positive photographic silver halide emulsions of this invention can comprise silver halide grains which are cubic-regular. To illustrate, the following photographic silver halide emulsions are prepared:

Emulsion A

A conventional direct-positive photographic silver bromoiodide emulsion, containing approximately 2 mole percent iodide and having an average grain size of about 0.25 micron, is prepared using the procedure described for Emulsion No. 9 in the Trivelli and Smith article entitled, "Empirical Relations Between Sensitometric and Size-Frequency Characteristics in Photographic Emulsion Series," published in The Photographic Journal, vol. LXXIX, May 1939 (pp. 330–338), except that the emulsion is not chemically sensitized, i.e., the second ripening is omitted. As shown by electron micrographs, there are substantially no regular silver halide grains in the emulsion. This emulsion is reduction and gold fogged by adding thiourea dioxide (0.4 mg. per mole of silver halide), heating for 80 minutes at 65° C., and then adding potassium chloroaurate (2 mg. per mole of silver halide) and heating for 40 minutes at 65° C. 100 mg. of an electron accepting compound (5-m-nitrobenzylidenerhodanine) per mole of silver halide is added and the emulsion is coated on conventional cellulose acetate film support at a coverage of 100 mg. of silver and 315 mg. of gelatin per mole of silver halide.

Emulsion B

A cubic-regular direct-positive photographic silver bromoiodide emulsion containing approximately 2 mole percent iodide and having an average grain size of about 0.25 micron is prepared by adding (1) an aqueous solution of potassium bromide and potassium iodide and (2) an aqueous solution of silver nitrate, simultaneously to a rapidly agitated aqueous gelatin solution at a temperature of 55° C., over a period of about 33 minutes. The pH is maintained at about 2 during precipitation and the pAg at about 9. Over 95%, by weight, of the silver halide crystals have a cubic-regular shape. The emulsion is reduction and gold fogged by first adding thiourea dioxide (1 mg. per mole of silver halide) and heating for 60 minutes at 65° C., and then adding potassium chloroaurate (2 mg. per mole of silver halide) and heating for 40 minutes at 65° C. 100 mg. of an electron accepting compound (5-m-nitrobenzylidenerhodanine) per mole of silver halide is added and the emulsion is coated on conventional cellulose acetate film support at a coverage of 100 mg. of silver and 370 mg. of gelatin per square foot of support.

Samples of each of the coatings of Emulsions A and B are exposed on an Eastman Ib sensitometer, developed for 6 minutes in Kodak DK-50 developer, fixed, washed and dried. The maximum density, photographic speed at a given density below maximum density and gamma are determined using the same procedure for each coating. The results are as follows:

TABLE 2

| Emulsion coating | $D_{max}$ | Relative speed | Gamma |
|---|---|---|---|
| A | 1.5 | 100 | 1.0 |
| B | 2.2 | 795 | 3.0 |

It can be seen from the above results that the use of cubic regular silver halide grains in fogged direct-positive photographic silver halide emulsions gives a substantial increase in photographic speed. Similar increases in photographic speed are obtained when the above procedure is repeated with fogging agents such as hydrazine, tetra(hydroxymethyl)phosphonium chloride, triethylenetetramine and gold or noble metal fogging agents such as potassium aurithiocyanate, 2-aurosulfobenzothiazole metho chloride, and ammonium hexachloro palladate $[(NH_4)_2PdCl_6]$ and the like.

EXAMPLE III

As previously indicated, the regular silver halide grains which are fogged with a combination of a low concentration of reduction fogging agent and noble metal fogging agent are characterized by a rapid loss of fog upon chemical bleaching. To illustrate, a sample of Emulsion Coating B of Example II is bleached before development in a chemical bleach having the following composition:

Potasium cyanide—50.00 mg.
Acetic acid (glacial)—3.47 cc.
Sodium acetate—11.49 g.
Potassium bromide—119.00 mg.
Water to 1.0 liter.

The film sample is bleached for 10 minutes at 68° F., in the above bleach without agitation. The coating is then washed in running water for 10 minutes and allowed to dry at room temperature. The coating is then developed for 6 minutes in Kodak DK-50 developer, fixed, washed and dried in the conventional manner. The film sample exhibits a loss of over 45% in maximum density upon bleaching. In contrast, increasing the concentration of the thiourea dioxide to 1.5 mg. per mole of silver halide and the potasium chloroaurate to 15 mg. per mole of silver halide during the fogging step for Emulsion B gives a coating which exhibits a loss of less than 10% in maximum density upon bleaching. Furthermore, the use of stannous chloride and auric trichloride at the higher concentrations gives a coating for Emulsion B exhibiting a density loss of only 5% upon bleaching.

EXAMPLE IV

Color forming couplers can be incorporated into the direct-positive photographic silver halide emulsions described herein. To illustrate, the dyes indicated in the following Table 3 are added to samples of the reduction and gold fogged cubic regular silver bromoiodide emulsion of Example II which contains the electron acceptor 5-m-nitrobenzylidenerhodanine. (Emulsion B), and the emulsion is digested for 10 minutes at 52° C. Coupler dispersions melted at 40° C., are added to the emulsion where indicated in the following Table 3. The emulsions are cooled to 40° C., and coated on conventional cellulose acetate film support, as in Example II. The film coatings are exposed and processed as indicated in the following table to give reversal images in color.

TABLE 3

| Coating | Dye (g./mole) | Region of sensitization | Color forming coupler | Exposure | Color of dye formed by coupler | Type of process |
|---|---|---|---|---|---|---|
| 1 | None | Blue | α-benzoyl-3-[α-(2,4-di-amylphenoxy)butyramido]-2-methoxyacetanilide | Tungsten source Wratten No. 35+38A filters. | Yellow | A |
| 2 | Anhydro-1'-ethyl-3(3-sulfobutyl)thia-2'-cyanine hydroxide (0.2) + Anhydro-1-ethyl-1'-(4-sulfobutyl)-2,2'-cyanine hydroxide (0.2). | Green | 1-(2,4,6-trichlorophenyl)-3,3'-(2'',4''-di-t-amylphenoxy-acetamido) benzimidazo-5-pyrazolone. | Tungsten source Wratten No. 61+16 filter. | Magenta | A |
| 3 | 3,3'-dimethyl-8,10-di (m-toloxy)thiacarbocyanine bromide (0.2). | Red | 5[α- (2,4-di-t-amylphenoxy)hexanamido]-2-heptafluorobutyramidophenol 1-Hydroxy-2[α- (2,4-di-t-amylphenoxy-n-butyl)]napthamide. | Tungsten source Wratten No. 29 filter. | Cyan | A |
| 4 | 3,3'-dimethyl-8,10-di-(m-toloxy)thiacarbocyanine bromide (0.2) | Red | 1-hydroxy-2-[β-(2-acetamido)-phenethyl]-naphthalamide | Daylight quality source Wratten No. 16 filter | Cyan | B |

A-Reversal color process as described in Graham et al. U.S. Patent, 3,046,129, issued July 24, 1962 in Example (a) (col. 27, lines 25 et seq.) except that black-and-white (MQ) development is omitted and the color development is reduced to 1 minute and done in total darkness until after fixing.
B-Color process for developing cyan dye images as described in Vittum et al U.S. Patent 3,002,836 issued October 3, 1961 in Example III (col.4, lines 45 et seq.) except that black-and-white (MQ) development is omitted.

EXAMPLE V

The following photographic silver halide emulsions are prepared:

Emulsion A

A direct-positive photographic silver bromoiodide emulsion containing approximately 2.5 mole percent iodide and having an average grain size of about 0.25 micron is prepared by adding an aqueous solution of silver nitrate to a rapidly agitated aqueous solution of gelatin, potassium bromide and potassium iodide at a temperature of about 40° C., over a period of about 5 minutes. The pH is raised to about 8.5 with ammonia (28 percent aqueous solution) and the emulsion is held for 5 minutes at 40° C. The pH is adjusted to 6.2 with sulfuric acid and the emulsion is chill-set, noodled and washed in the conventional manner. The emulsion comprises silver halide grains of odd shape, e.g., flat triangles, needles, etc., having (1,1,1) twin plane stacking faults and substantially no regular silver halide grains. The emulsion is reduction and gold fogged by first adding thiourea dioxide (1.5 mg. per mole of silver halide) and heating for 60 minutes at 65° C., and then adding potassium chloroaurate (3 mg. per mole of silver halide) and heating for 30 minutes at 65° C. 100 mg. of an electron accepting compound such as 3,3'-di-o-nitrophenylthiacarbocyanine perchlorate, per mole of silver halide is added to the emulsion which is then coated on cellulose acetate film support at a coverage of 100 mg. of silver and 340 mg. of gelatin per square foot of support.

Emulsion B

A cubic-regular directive-positive photographic silver bromoiodide emulsion containing approximately 2.5 mole percent iodide and having an average grain size of about 0.25 micron is prepared by adding (1) an aqueous solution of potassium bromide and potassium iodide and (2) an aqueous solution of silver nitrate simultaneously to a rapidly agitated aqueous gelatin solution at a temperature of 70° C., over a period of about 35 minutes. The pH is maintained at about 2 during precipitation and the pAg at about 9. The photographic emulsion is cooled to 40° C., and sufficient gelatin added to give an 8 percent gelatin solution. The photographic emulsion is then chill-set, shredded and washed in the conventional manner. The silver halide grains in the emulsion are substantially cubic and are free of twin plane stacking faults. The emulsion is reduction and gold fogged by first adding thiourea dioxide (0.5 mg. per mole of silver halide) and heating for 60 minutes at 55° C., and then adding potassium chloroaurate (1.5 mg. per mole of silver halide) and heating for 10 minutes at 65° C. 100 mg. of an electron accepting compound such as 3,3'-di-o-nitrophenylthiacarbocyanine perchlorate per mole of silver halide is added to the emulsion. The emulsion is then coated on cellulose acetate film support at a coverage of 100 mg. of silver and 370 mg. of gelatin per square foot of support.

Samples of each of the coatings of Emulsions A and B are exposed on an Eastman Ib sensitometer, developed for 6 minutes in Kodak DK-50 developer, fixed, washed and dried. The maximum density, photographic speed at a given density below maximum density and gamma are determined using the same procedure for each coating. The results are as follows:

TABLE 4

| Emulsion coating | $D_{max}$ | Relative speed | Gamma |
|---|---|---|---|
| A | 1.8 | 100 | 1.5 |
| B | 2.3 | 398 | 3.0 |

From the above table it can be seen that the fogged directive-positive regular silver halide emulsions of this invention give higher speeds. $D_{max}$ and gamma than do the fogged direct-positive photographic silver halide emulsions comprising conventional silver halide grains. Similar results are obtained when the above procedure is repeated with direct-positive photographic silver bromide or silver chlorobromide emulsions containing regular grains.

EXAMPLE VI

As previously indicated, a preferred direct-positive photographic silver halide emulsion of this invention comprises regular silver halide grains which are reduction and gold fogged with a low concentration of reduction fogging agent. In such a procedure it is most desirable to also employ a relatively low concentration of gold fogging agent since increasing concentrations of gold fogging agent generally decrease photographic speed. To illustrate, the cubic regular silver bromoiodide emulsion of Example II (Emulsion B) is reduction fogged by first adding 0.25 mg. of thiourea dioxide per mole of silver halide and heating the emulsion for 60 minutes at 65° C. This emulsion is then divided into several portions and varying concentrations of potassium chloroaurate, as listed in the following Table 5, are added to each portion of the emulsion and each portion is heated for 60 minutes at 65° C. 500 mg. per mole of silver halide of an electron accepting compound which is an imidazoquinoxaline dye of the type disclosed in Brooker et al., Belgian Patent 660,253, published Mar. 15, 1965, is added to each portion of the emulsion. A sample of each portion of the emulsion is coated on a cellulose acetate film support at a coverage of 100 mg. of silver and 250 mg. of gelatin per square foot of support. A sample of each coating is exposed and processed as in Example II. The following results are obtained:

TABLE 5

| Coating No. | Potassium chloroaurate (mg./mole AgX) | Relative speed |
|---|---|---|
| 1 | 6 | 100 |
| 2 | 4 | 178 |
| 3 | 2 | 224 |

Prior art direct-positive photographic silver halide emulsions comprising conventional silver halide grains which are fogged with a combination of a reducing agent and a gold compound or a compound of a metal more electro-positive than silver, as described in British Patent 723,019, exhibit only low photographic speed, for example, photographic speed comparable to that of photographic emulsions used in conventional enlarging papers. Such a photographic speed, on the relative scale set forth in the above Table 5, is only 10. Thus, it can be seen that the direct-positive photographic silver halide emulsions disclosed herein exhibit a truly outstanding increase in photographic speed in comparison to such prior art direct-positive photographic silver halide emulsions.

EXAMPLE VII

The direct-positive photographic silver halide emulsions of this invention can be blended to modify photographic properties. For example, such blends can exhibit wider exposure latitude and lower contrast. To illustrate this feature of the invention, three cubic regular direct-positive photographic silver halide emulsions containing approximately 2.5 mole percent iodide are prepared using the procedure of Example II. Emulsion B except that the reacting potassium and silver solutions are mixed over a period of about 35 minutes and the temperature is varied as indicated in the following Table 6. The cubic regular photographic silver bromoiodide emulsions obtained (Emulsions A, B and C in the following Table 6) are reduction and gold fogged and the electron acceptor (5-m-nitrobenzylidenerhodanine) is added as in Example II, Emulsion B. The resulting emulsions are coated on conventional cellulose acetate film support at coverages of 100 mg. of silver and 150 mg. of gelatin per square foot of support. Samples of the emulsions are also blended (Emulsion D in the following Table 6), and the blend coated at the same coverages on cellulose acetate film base.

Samples of each of the coated direct-positive emulsions are exposed on an Eastman Ib sensitometer, developed for 6 minutes in Kodak D-19 developer, fixed, washed and dried. The maximum density, photographic speed at a density of 1.0 gamma are determined using the same procedure for each coating. The results are as follows:

TABLE 6

| Emulsion | Temperature (° C.) | Average grain size (μ) | Blend components (mole percent) | $D_{max}$ | Gamma | Relative speed |
|---|---|---|---|---|---|---|
| A | 70 | 0.22 | — | 2.0 | 2.3 | 1600 |
| B | 55 | 0.17 | — | 2.0 | 3.0 | 400 |
| C | 40 | 0.12 | — | 2.0 | 4.0 | 100 |
| D | — | — | A (45), B (32), C (23) | 2.0 | 1.0 | 400 |

Thus, by the practice of this invention there is provided direct-positive photographic silver halide emulsions exhibiting excellent photographic speed. Such emulsions are preferably prepared using gold fogging agents in combination with reduction fogging agents at low concentrations. Due to their increased photographic speed, the direct-positive photographic silver halide emulsions disclosed herein are particularly useful in a variety of applications in the photographic field. For example, they can be used in lithographic printing plates, particularly those of the type disclosed in U.S. Patent 3,146,104, issued Aug. 25, 1965, in color transfer materials, direct reversal color processes, duplicating film, e.g., microfilm, etc. If desired, the silver halide grains can be gold fogged using special processing techniques, for example, a coating of a reduction fogged silver halide emulsion containing an electron accepting compound can be exposed and bathed in a solution of a gold salt such as gold thiocyanide which can contain a small concentration, for example, less than about 0.5%, of a halogen such as bromide. The coating can then be processed in an alkaline developer such as Kodak DK-50 or Kodak DK-19 developer for 5–10 minutes at 68° F. Another interesting reversal system involves developing, in a fogging developer, a photographic silver halide emulsion which has been treated with a reduction fogging agent such as stannous chloride. This system involves exposing and developing the aforesaid photographic emulsion in an alkaline fogging developer such as Kodak DK-50 developer to which small concentrations, for example, up to about 0.2 gram per liter of triethylenetetramine and 1-phenyl-3-pyrazolidone have been added to obtain a reversal image.

The fogged direct-positive photographic silver halide emulsions described herein can also be used in negative azo dye image formation. The art of bleaching an azo dye by chemistry involving the oxidation of metallic silver is well known. In such methods an azo dye in a coating containing a stepwise image of metallic silver is bleached proportional to the silver under strongly acidic conditions giving a reversal image in dye. Bleaching rates are enhanced by accelerators such as 2-hydroxy-3-amino phenazine or anthraquinone-beta-sulfonic acid as shown, for example, at page 643 of Photographic Chemistry, English language edition, vol. 2 by Pierre Glafkides. This type of bleaching process can employ a very fine grain direct-positive photographic silver halide emulsion of the type described herein. Exposure, development in an alkaline developer such as Kodak DK-50 developer and fixation give a direct-positive silver image with no effect on the azo dye. Conventional dye bleaching, silver bleaching and fixation then give a dye image reversal of the silver image and also a dye reversal of the original subject with an excellent ratio of D max. to D min.

As shown herein, color forming couplers can be incorporated into the direct-positive photographic silver halide emulsions of this invention. It has been found that the incorporation of a color forming coupler or coupler solvent in the emulsion significantly improves the quality of the reversal obtained in black and white elon-hydro-quinone type developers. There is obtained an increase in contrast and a lower minimum density using this type developer with such emulsions.

The fogged, direct-positive photographic silver halide emulsions of this invention can also be used in color difussion transfer systems in combination with dye developers. Photographic developers which contain a dye moiety can, of course, be synthesized. Upon applying an alkaline solution to an imagewise exposed negative developing silver halide emulsion element containing one of these dye developers, the dye developer becomes immobilized within the element where development occurs, that is, in the exposed areas. When an alkaline treated sample of this material is brought into contact with a receiver sheet, there is obtained a positive transfer print composed of transferred dye-developer and a negative print composed of non-transferred dye developer when the negative silver image is bleached. Dye developer coatings made with a reversal emulsion of the type disclosed herein will develop to yield a positive silver image. Therefore, an alkaline treated sample of this material brought in contact with a receiver will yield a negative dye transfer print composed of transferred dye-developer and a positive print composed of non-transferred dye developer when the positive silver image is bleached.

The fogged, direct-positive photographic silver halide emulsions of this invention can also be used in reversal chemical transfer systems. The chemical transfer system is often used for making positive copies from positive originals and is very popular since stable right-reading images are readily obtained. The negative is exposed in a normal manner, then passed through a solvent developer in contact with a nucleated receiver. The exposed negative silver is developed, while the unexposed silver halide dissolves and diffuses to the receiver sheet where it is deposited on the nuclei and developed. The chemical transfer print can be obtained in a short time since no additional processing steps are necessary. The fogged, direct-positive photographic silver halide emulsions of this invention, upon exposure to a negative image followed by development, give a negative silver image in the emulsion layer. In the presence of a solvent developer, the exposed silver halide which has not developed, migrates to the nucleated receiver where it is deposited as a positive image. The emulsions of this invention can be used in chemical transfer processes employed to make a chemical transfer print by either the one-sheet system, in which the emulsion is coated on the same support as the receiver layer, or by the two-sheet system, in which the emulsion and receiver layers are coated on separate supports.

The direct-positive photographic silver halide emulsions of this invention can also be processed in the presence of ammonia vapors or other gaseous compounds of the type disclosed in U.S. Patent 3,158,481, issued Nov. 24, 1964; U.S. Patent 3,144,334, issued Aug. 11, 1964; and British Patent 973,965, published Nov. 4, 1964. The developing agent can be incorporated into the emulsion coating or in a separate sheet. Ammonia or another gaseous compound which is used to activate the coating can be incorporated in a separate layer of the element containing the emulsion. The ammonia or other activator can be in any suitable form, for example, in the form of an ammonia polymer. Such activating materials can also be incorporated in a sheet separate from the element containing the emulsion and activated by heat. Processing with ammonia or other activators is of special interest in the document copying field where the emulsion is coated on paper or as a film duplicating material where the emulsion is coated on film.

Certain of the direct-positive photographic silver halide emulsions of this invention are capable of being used as a negative material by increasing exposure. Thus, a fine grain cubic regular silver bromide photographic emulsion which has been reduction and gold fogged using low concentrations of the fogging agents, as disclosed herein can be first treated with an electron accepting compound and subsequently treated with an orthochromatic sensitizing dye such as a thiazoline-rhodanine merocyanine to obtain a suitable photographic emulsion for this purpose. The orthochromatic sensitizing dye is generally used in a concentration substantially in excess of the electron accepting compound, e.g., it is generally used at a concentration which is about double the concentration of the electron accepting compound. When exposed in the projection speed range such an emulsion gives a direct-positive image. Upon increasing exposure a negative image is produced.

Although the invention has been described in considerable detail with reference to certain preferred embodiment thereof, it will be understood that variations and modifications can be effected without departing from the spirit and scope of the invention as described hereinabove and as defined in the appended claims.

We claim:

1. A regular grain direct-positive photographic silver halide emulsion comprising *reduction and gold* fogged silver halide grains wherein the halide of said silver halide grains is at least 50 mole percent bromide and wherein said emulsion comprises an organic desensitizer compound having an anodic polarographic half-wave potential and a cathodic half-wave potential which, when added together, give a positive sum.

2. A regular grain direct-positive photographic silver halide emulsion comprising *reduction and gold* fogged silver halide grains wherein the halide of said silver halide grains comprises less than about 10 mole percent iodide and wherein said emulsion comprises an organic desensitizer compound having an anodic polarographic half-wave potential and a cathodic half-wave potential which, when added together, give a positive sum.

3. An emulsion according to claim 2 wherein at least 80% by weight, of said grains are regular.

[4. An emulsion according to claim 2 wherein said silver halide grains are reduction and gold fogged.]

5. The photographic emulsion of claim 2 in which said silver halide grains are fogged with about 0.00005 to about 0.06 milliequivalent per mole of silver halide of a reduction fogging agent and about 0.001 to about 0.01 millimole per mole of silver halide of a gold fogging agent.

6. The photographic emulsion of claim 2 in which said desensitizer is an organic compound which spectrally sensitizes in the range of about 480 to about 800 mμ.

7. The photographic emulsion of claim 5 in which the ratio of gold fogging agent to reduction fogging agent is in the range of about 1:3 to about 20:1.

8. The photographic emulsion of claim 2 in which the silver halide comprises at least 50 mole percent bromide and said desensitizer is a cyanine dye.

9. The photographic emulsion of claim 2 which contains a spectral sensitizing dye in addition to said desensitizer.

10. The direct-positive photographic silver halide emulsion of claim 2 in which no more than about 20%, by number, of any silver halide grains larger in size than the mean grain size are not regular.

11. A photographic element comprising a support and at least one direct-positive photographic silver halide layer which comprises *reduction and gold* fogged silver halide grains wherein at least 80%, by weight, of said grains are regular, wherein the halide of said silver halide grains is at least 50 mole percent bromide and wherein said emulsion comprises an organic desensitizer compound having an anodic polarographic half-wave potential and a cathodic half-wave potential which, when added together, give a positive sum.

12. A photographic element comprising a support and at least one direct-positive photographic silver halide layer which comprises *reduction and gold* fogged silver halide grains wherein the halide of said silver halide grains is less than 10 mole percent iodide and wherein said emulsion comprises an organic desensitizer compound having an anodic polarographic half-wave potential and a cathodic half-wave potential which, when added together, give a positive sum.

[13. A photographic element according to claim 11 wherein said fogged silver halide grains are reduction and gold fogged.]

14. The photographic element of claim 11 in which said desensitizer is an imidazoquinoxaline dye.

15. The photographic element of claim 11 in which said silver halide grains are fogged with about 0.0005 to about 0.06 milliequivalent per mole of silver halide of a reduction fogging agent and about 0.001 to about 0.01 millimole per mole of silver halide of a gold fogging agent, the ratio of gold fogging agent to reduction fogging agent being in the range of about 1:3 to about 20:1.

16. The photographic element of claim 12 in which the silver halide grains are cubic-regular grains having a mean grain size in the range of about 0.1 to about 2 microns, and said grains in said emulsion being such that a test portion thereof, when coated as a photographic silver halide emulsion on a support to give a maximum density of at least about 1 upon processing for 6 minutes at about 68° F. in Kodak DK-50 developer, has a maximum density which is at least about 30% greater than the maximum density of an identical coated test portion which is processed for 6 minutes at about 68° F. in Kodak DK-50 developer after being bleached for about 10 minutes at about 68° F. in a bleach composition of:

potassium cyanide—50 mg.
acetic acid (glacial)—3.47 cc.
sodium acetate—11.49 g.
potassium bromide—119 mg.
water to 1 liter.

17. The photographic element of claim [13] *11* in which the reduction fogging agent is thiourea dioxide and the gold fogging agent is potassium chloroaurate.

18. The photographic element of claim 15 in which the reduction fogging agent is thiourea dioxide and the gold fogging agent is potassium chloroaurate.

19. The process which comprises contacting (1) silver halide grains, at least 80%, by weight, of which are regular with (2) about 0.0005 to about 0.06 milliequivalent per mole of silver halide of a reduction fogging agent and about 0.001 to about 0.01 millimole per mole of silver halide of a gold fogging agent (3) at a temperature in the range of about 40 to about 100° C., the ratio of gold fogging agent to reduction fogging agent being in the range of about 1:3 to about 20:1.

20. The process of claim 19 in which the silver halide comprises at least 50 mole percent bromide and has a mean grain diameter in the range of about 0.1 to about 2 microns.

21. The process of claim 19 in which the silver halide grains are contacted with the reduction fogging agent and are subsequently contacted with the gold fogging agent.

22. The process of claim 9 in which the reduction fogging agent is thiourea dioxide and the gold fogging agent is potassium chloroaurate.

23. The process of claim 19 comprising adding a desensitizer having an anodic polarographic half-wave potential and a cathodic half-wave potential which, when added together, give a positive sum, to the silver grains after they have been contacted with the reduction and gold fogging agents.

*24. A cubic regular grain direct-positive silver halide emulsion comprising reduction and gold fogged silver halide grains wherein the halide of said cubic regular silver halide grains is at least 50 mole percent bromide and wherein said emulsion comprises an organic desensitizer compound having an anodic polarographic half-wave potential and a cathodic half-wave potential which, when added together, give a positive sum.*

*25. A cubic regular grain direct-positive silver halide emulsion according to claim 24 wherein the cubic regular silver halide grains are less than 10 mole percent iodide.*

*26. A cubic regular grain direct-positive silver halide emulsion according to claim 25 wherein the cubic regular silver halide grains are silver bromoiodide grains.*

*27. A cubic regular grain direct-positive silver halide emulsion according to claim 24 in which no more than about 20 percent, by number, of any silver halide grains larger in size than the mean grain size are not regular.*

*28. A cubic regular grain direct-positive silver halide emulsion according to claim 24 wherein at least 80 percent by weight of said silver halide grains are regular.*

*29. A cubic regular grain direct-positive silver halide emulsion according to claim 24 wherein said desensitizer is a cyanine dye.*

*30. A cubic regular grain direct-positive silver halide emulsion according to claim 24 wherein said desensitizer is an imidazoquinoxaline dye.*

*31. A photographic element comprising a support and at least one direct-positive photographic silver halide layer which comprises reduction and gold fogged silver halide grains wherein at least 80 percent, by weight, of said grains are cubic regular, wherein the halide of said cubic regular silver halide grains is at least 50 mole percent bromide and less than 10 mole percent iodide and wherein said emulsion*

*comprises an organic desensitizer compound having an anodic polarographic half-wave potential and a cathodic half-wave potential which, when added together, give a positive sum.*

*32. A photographic element according to claim 31 wherein the cubic regular silver halide grains are silver bromoiodide grains.*

*33. A photographic element comprising a support and at least one direct-positive photographic silver halide layer which comprises reduction and gold fogged cubic regular silver halide grains wherein no more than 20 percent, by number, of any silver halide grains larger in size than the mean grain size are not cubic regular, the halide of said cubic regular silver halide grains is at least 50 mole percent bromide and less than 10 mole percent iodide and wherein said emulsion comprises an organic desensitizer compound having an anodic polarographic half-wave potential and a cathodic half-wave potential which, when added together, give a positive sum.*

*34. A photographic element according to claim 33 wherein the cubic regular silver halide grains are silver bromoiodide grains.*

*35. A photographic element according to claim 33 wherein said desensitizer is a cyanine dye.*

* * * * *

UNITED STATES PATENT AND TRADEMARK OFFICE

CERTIFICATE OF CORRECTION

PATENT NO. : Re 29,575

DATED : Reissued March 14, 1978

INVENTOR(S) : Bernard D. Illingsworth, deceased

It is certified that error appears in the above-identified patent and that said Letters Patent are hereby corrected as shown below:

Column 4, line 65, "filed" should read --issued--. Column 7, line 12, that part of the formula reading "6,6α" should read --6,6'--; line 25, that part of the formula reading "CH=CH-CH-" should read -- CH=CH-CH= --; line 45, that part of the formula reading "CH=CH-CH=" should read -- CH=CH-C= --; line 67, that part of the formula reading "6,6α" should read --6,6'--. Column 8, line 19, that part of the formula reading "(4- -nitrophenyl)- 5" should read --(4-nitrophenyl)-5--. Column 9, line 12, "examplified" should read --exemplified--; line 40, "e.g." should read --i.e.--. Column 12, line 63, the "." after 5-m-nitrobenzylidenerhodanine should be --, --. Column 14, line 53, "speeds" should read --speed--. Column 15, line 41, "electro-positive" should read --electropositive--; line 61, "II." should read --II,--. Column 17, lines 17-18, "elon-hydroquinone type" should read --Elon-hydroquinone-type--. Column 19, line 35, before "wherein", --wherein at least 80%, by weight, of said grains are regular,-- should be inserted. Column 20, line 27, "9" should read --19--.

Signed and Sealed this

*Sixteenth* Day of *January 1979*

[SEAL]

*Attest:*

RUTH C. MASON
*Attesting Officer*

DONALD W. BANNER
*Commissioner of Patents and Trademarks*